(12) United States Patent
Taupin et al.

(10) Patent No.: US 6,685,963 B1
(45) Date of Patent: Feb. 3, 2004

(54) DIPHASIC INJECTION COMPOSITION CONTAINING DISPERSED AND CONTINUOUS PHASES USEFUL FOR REPARATIVE AND PLASTIC SURGERY

(75) Inventors: Valérie Taupin, Courbevoie (FR); Estelle Piron, Pringy (FR); Raymonde Tholin, Annecy (FR); Franck Villain, Annecy (FR)

(73) Assignees: Corneal Industrie, Pringy (FR); Dermatech, Paris (FR)

( * ) Notice: Subject to any disclaimer, the term of this patent is extended or adjusted under 35 U.S.C. 154(b) by 0 days.

(21) Appl. No.: 09/720,936

(22) PCT Filed: Jun. 30, 1999

(86) PCT No.: PCT/FR99/01568

§ 371 (c)(1),
(2), (4) Date: Jan. 2, 2001

(87) PCT Pub. No.: WO00/01428

PCT Pub. Date: Jan. 13, 2000

(30) Foreign Application Priority Data

Jul. 1, 1998 (FR) .............................................. 98 08386

(51) Int. Cl.$^7$ .................................................. A61K 9/14
(52) U.S. Cl. ....................... 424/486; 424/487; 424/488; 424/423
(58) Field of Search ................................ 435/174, 177; 424/502, 488, 487; 514/1

(56) References Cited

U.S. PATENT DOCUMENTS

| | | | | |
|---|---|---|---|---|
| 4,433,073 A | * | 2/1984 | Sano et al. .................. | 523/201 |
| 4,654,039 A | * | 3/1987 | Brandt et al. ............... | 604/368 |
| 5,922,507 A | * | 7/1999 | Van Damme et al. ... | 430/273.1 |

FOREIGN PATENT DOCUMENTS

| | | | |
|---|---|---|---|
| EP | 0826381 A2 | * | 4/1998 |
| WO | 96/33751 | * | 10/1996 |
| WO | WO 96/33751 | * | 10/1996 |

* cited by examiner

Primary Examiner—David M. Naff
Assistant Examiner—Deborah K. Ware
(74) Attorney, Agent, or Firm—Klauber & Jackson

(57) ABSTRACT

Biocompatible diphasic compositions are prepared comprising a dispersed phase suspended in a continuous phase, more particularly suitable for use as a filling material in reparative and plastic surgery. The dispersed phase consists of particles of at least one hydrogel of a (co)polymer obtained by polymerizing and cross-linking acrylic acid, methacrylic acid and/or at least one derivative of said acids. The continuous phase is an aqueous solution or hydrogel of a polymer selected from proteins, polysaccharides and their derivatives which have been cross-linked. The polysaccharide may be hyaluronic acid, its salts and a mixture of its salts, advantageously consisting of a sodium hyaluronate.

24 Claims, No Drawings

DIPHASIC INJECTION COMPOSITION CONTAINING DISPERSED AND CONTINUOUS PHASES USEFUL FOR REPARATIVE AND PLASTIC SURGERY

The present invention has for its principal object diphasic injectable compositions, in particular useful in reparative and plastic surgery. It has more precisely for object:

- biocompatible diphasic compositions comprising a dispersed phase in suspension in a continuous phase;
- a method for preparing said compositions;
- a filling material useful in reparative surgery and in plastic surgery, based on said diphasic compositions.

The present invention proposes in particular a satisfactory solution to the technical problem of durable filling of the defects of volume of the skin, such as wrinkles or scars, particularly on the face.

With reference to this technical problem, different approaches and in particular different diphasic injection compositions have already been proposed according to the prior art.

As from 1970, Jaime Planas had the idea to make particles of silicone, in order to inject them under the skin.

More precisely, it has been described:

- in EP-A-0 406 375: an alloplastic implant based on a histocompatible solid: said pulverulent solid being constituted by solid particles of diameter included on average between 10 μm and 200 μm, and which present a smooth surface having no angle nor edge. A product which corresponds to this Patent Application is found at present on the market. Said product, marketed under the Trademark Artecoll®, consists of microspheres of polymethacrylate (PMMA) in suspension in a collagen solution;
- in EP-A-0 466 300: a viscoelastic gel comprising a gelatinous phase (having undergone a low-rate cross-linking) dispersed in a liquid phase (not having undergone cross-linking); said two phases advantageously having been prepared from fibers of Hylan (natural hyaluronic acid chemically modified in situ for the purpose of facilitating extraction thereof from the tissues);
- in U.S. Pat. No. 5,137,875: injectable solutions or dispersions of collagen, containing hyaluronic acid in solution;
- in WO-A-96 33751: diphasic compositions capable of containing in their continuous and dispersed phases hyaluronic acid or one of its salts; said acid or salt intervening, "relatively" cross-linked in the form of fragments, in order to constitute the dispersed phase, and in aqueous solution, not or very little cross-linked, in order to constitute the continuous phase. It is provided to employ in said continuous phase, in combination or in place of said hyaluronic acid or one of its salts, another biocompatible polymer selected from proteins, polysaccharides and derivatives thereof.

Furthermore, a product, of the diphasic composition type, would be evaluated in the United States. It is principally constituted by silicone balls, dispersed in a solution of polyvinylpyrrolidone.

Incidentally, it will be noted here that documents EP-A-826 381, FR-A-2 568 127, U.S. Pat. No. 4,657,553 and U.S. Pat. No. 4,563,490 do not describe diphasic compositions.

There are therefore numerous variants of diphasic compositions, useful in reparative and plastic surgery and it does not appear obvious to develop one of them, optimalized with reference to the numerous parameters consisting of:

- the exact nature and form of the continuous phase;
- the nature, form, surface state . . . of the dispersed phase.

In such a context, Applicants propose a novel type of diphasic composition which shows particularly high-performance.

The biocompatible diphasic composition of the type of the invention therefore includes a dispersed phase suspended in a continuous phase and, characteristically, said dispersed phase consists of particles of at least one hydrogel of a (co)polymer obtained by polymerizing and cross-linking acrylic acid and/or methacrylic acid and/or at least one derivative of said acids.

The diphasic compositions of the invention are injectable compositions. They have been formulated with this in view. It is particularly for that purpose that they contain a continuous phase; said phase serving as injection vehicle for the particles of the dispersed phase.

The term injectable used in the present text means manually injectable by means of syringes provided with conventional needles. The diphasic compositions of the invention are particularly interesting in that they can be formulated to be injectable by means of very fine needles (with a diameter included between 0.3 and 0.5 mm). The person skilled in the art understands that the determining parameter is that of the largest dimension of the particles in suspension. Within the framework of the present invention, it is in particular possible to formulate compositions injectable through hypodermic needles of 30 G ½, 27 G ½, 26 G ½, 25 G. Said compositions constitute the most advantageous variant of the compositions of the invention.

The injectable diphasic compositions of the invention are more particularly intended for dermic injection (superficial, mean or deep) for an implantation in the dermis. To that end, for the purpose of eliminating any unpleasant feeling or any pain during their injection and during their implantation, they are advantageously buffered at a pH included between 6.5 and 7.5, preferably included between 7 and 7.4, and preferably still, between 7.2 and 7.3.

In this way, the two continuous and dispersed phases of said diphasic compositions are advantageously buffered at that pH.

A phosphate buffer is generally employed.

The diphasic compositions of the invention therefore comprise an original dispersed phase as specified hereinabove, suspended in an adequate continuous phase.

Said continuous phase must, in effect, be capable of performing several functions, and in particular:

a) it must maintain the dispersed phase in suspension, in stable manner, b) it must constitute a high-performance injection vehicle, c) after injection and implantation of the diphasic composition, it must advantageously protect said dispersed phase (in particular prevent it from migrating and promote the formation of fibroblasts around its particles, which slows down degradation thereof).

With reference to points a and b, it will be understood that a compromise must be adopted. Said continuous phase must be sufficiently fluid to be able to be easily injected, and sufficiently viscous to avoid decantation of the dispersed phase.

The compromise mentioned hereinbefore may be obtained with different types of continuous phase. Within the framework of the invention, certain types, specified hereinafter, are largely preferred.

We now propose to give precisions on each of the phases—continuous phase, dispersed phase—of the diphasic compositions of the invention.

By way of continuous phase, an aqueous solution of at least one polymer selected from proteins, polysaccharides and their derivatives, cross-linked or not, is advantageously employed. Said polymer, depending on its nature, in order to perform the above-recalled functions, is capable of intervening not cross-linked, slightly cross-linked or strongly cross-linked. Collagen, albumin, elastin . . . may in particular be employed as protein; as polysaccharide or derivative of polysaccharide:hyaluronic acid, its salts, sulphates of chondroitine, keratane, heparin, alginic acid, starch, carboxymethylcellulose, chitosane.

The possible cross-linking of this type of polymer does not raise particular difficulties for the person skilled in the art.

It is more particularly recommended to employ "an aqueous solution" of a polymer selected from hyaluronic acid, its salts and mixtures of its salts; said polymer advantageously being cross-linked. In fact, according to a preferred variant, said continuous phase of the diphasic compositions of the invention is a hydrogel of a cross-linked polymer selected from hyaluronic acid, its salts and mixtures of its salts; said cross-linked polymer advantageously consisting of a sodium hyaluronate.

The term hyaluronic acid is used in the following text as generic name to designate both hyaluronic acid per se and its salts or mixtures of salts and in particular salts of hyaluronate. The diphasic compositions of the invention advantageously contain sodium hyaluronate in their continuous phase, by way of polymer selected from hyaluronic acid, its salts and mixtures of its salts. It is already specified that said sodium hyaluronate employed is advantageously of bacterial origin.

Said hyaluronic acid (or at least one of its salts) has been more especially retained in view of its advantageous properties. It may in particular be obtained by the bacterial route, by cellular route (therefore bereft of any contaminant of virus type or prions). It presents both a strong gelatinous nature, a noteworthy lubricating power, a good biocompatibility and a good hold in the organism. Moreover, it is easily cross-linkable.

Cross-linked, it is capable of presenting the viscosity required within the context of the invention and, in any case, it is more resistant to degradation and to heat (the latter point is not negligible insofar as the compositions of the invention are generally sterilized in an autoclave).

Characteristically, the continuous phase of the compositions of the invention is advantageously based on cross-linked hyaluronic acid. It is no longer really question of an aqueous solution but of a hydrogel. Said hyaluronic acid has been conventionally cross-linked with the aid of at least one cross-linking agent. In order to obtain a hydrogel containing a reasonable quantity of said cross-linking agent, it is recommended to use as starting material a hyaluronic acid whose molecular mass is greater than or equal to 1 million Daltons. According to an advantageous variant, it is recommended to use a hyaluronic acid whose molecular mass is included between 2 and 4 million Daltons. Furthermore, it is recommended to carry out said cross-linking via the hydroxy functions of the hyaluronic acid, by means of a cross-linking agent (at least one), under conditions which lead to a cross-linking rate of said hyaluronic acid (starting material) characterized by the ratio: total number of reactive functions of said cross-linking agent/total number of disaccharide repeating units of the molecules of hyaluronic acid present, included between 0.25 and 0.50.

In fact, the network of the hydrogel, which thus constitutes the continuous phase of the diphasic compositions of the invention, is based on molecules of hyaluronic acid joined by bridges of molecules of cross-linking agent; each of the disaccharide repeating units of said molecules of hyaluronic acid advantageously having between 0.25 and 0.50 of its hydroxy functions engaged in such bridges.

By way of cross-linking agent, any agent known for cross-linking the hyaluronic acid via its hydroxy functions—at least bifunctional cross-linking agent—and in particular a polyepoxide or its derivatives, may be employed. By way of such cross-linking agent, the following may in particular by employed: epichlorhydrin, divinylsulfone, 1,4-bis-(2,3-epoxypropoxy)butane (or 1,4-bis(glycidyloxy)butane or 1,4-butanediol diglycidyl ether=BDDE), 1,2-bis-(2,3-epoxypropoxy)ethylene, 1-(2,3-epoxypropyl)-2,3-epoxy cyclohexane . . . It is not excluded from the scope of the invention to employ a plurality of cross-linking agents . . . It is more particularly recommended to employ 1,4-butanediol diglycidyl ether (BDDE).

The person skilled in the art knows, in any case, how to master the cross-linking of hyaluronic acid.

The hydrogel constituting the continuous phase of the diphasic compositions of the invention, based on cross-linked hyaluronic acid, advantageously contains said cross-linked hyaluronic acid at a concentration included between 10 and 25 mg/g, advantageously between 15 and 25 mg/g. It may be specified here, in non-limiting manner, that said hydrogel in fact generally contains more than 95% by weight of water . . .

Incidentally, it is recalled here that the hyaluronic acid, from which the hydrogel constituting the continuous phase of the diphasic compositions of the invention is preferably elaborated, is advantageously obtained by the bacterial route (rather than by extraction from animal tissues, cockscomb and umbilical cords in particular . . . ) and that it is more particularly recommended to use a sodium hyaluronate. In fact, for elaborating said hydrogel the intervention of fibers of sodium hyaluronate, obtained by the bacterial route, is more particularly recommended.

The dispersed phase consists of particles of at least one hydrogel of a (co)polymer obtained by polymerizing and cross-linking acrylic acid and/or methacrylic acid and/or at least one derivative of said acids.

The size of said particles is conventionally more or less defined, insofar as:

they must not be too small: in such a hypothesis, they would be rapidly eliminated by the giant cells or the macrophages, they would migrate too easily and might thus develop a carcinogenic effect, and neither must they be too voluminous: in such a hypothesis, difficulties would be encountered in injecting them through hypodermic needles (such as needles 30 G ½ which present an internal diameter of 160 $\mu$m) and it is possible that they would not suit for filling wrinkles of small size . . . It will be noted here that, concerning the maximum size of said particles, their deformability which is more reduced in view of the material constituting them, than that of particles of other types, will be taken into account.

The largest dimension of said particles is generally included between 10 and 120 $\mu$m, advantageously between 20 and 80 $\mu$m.

One speaks of the largest dimension of said particles (i.e. of their equivalent diameter) insofar as it is advantageously question of fragments of hydrogel which present a rough surface, fragments of hydrogel generally obtained by crushing a mass of hydrogel.

It is in no way expressly excluded from the scope of the invention to employ particles with symmetry of revolution, presenting a smooth surface, bereft of angle and edge, but it is preferred by far to employ fragments such as specified hereinabove, fragments that may be obtained easily and which, a priori, present two advantages:

- a smooth implant surface has greater risks of provoking the formation of tumours than a rough surface (*Prog. Exp. Tumor Res.*, Vol. 5, pages 85–133: "Carcinogenesis through solid state surfaces" by F. BISCHOFF and G. BRYSON);
- a granulous particle surface promotes the growth of the fibrous tissues around, thus fixing the particles on the site of injection and avoiding their migration (*Cosmetics*, Vol. 100, No. 6, pages 1570–1574: "Bioplastique at 6 years", by ERSEK R. A., GREGORY S. R. and SALISBURY M. D.).

The fragments constituting the dispersed phase of the compositions of the invention may in fact present totally random shapes and in particular oval, rounded, triangular, square geometries . . . and even the form of sticks.

Said particles are particles of hydrogel. In that, they are in particular less traumatizing than particles of PMMA type of the prior art.

Said particles generally present, at equilibrium, a water content included between 10 and 40% by weight, advantageously close to 25% by weight.

Said hydrogel is a hydrogel of a methacrylic and/or acrylic, cross-linked, hydrophilic polymer or copolymer. It is obtained by polymerizing and cross-linking at least one monomer selected from acrylic acid, methacrylic acid and their derivatives.

Said hydrogel is advantageously obtained from at least one monomer selected from

| | |
|---|---|
| acrylic acid | methacrylic acid |
| ethyl acrylate | methyl methacrylate (MMA) |
| propyl acrylate | ethyl methacrylate (EMA) |
| n-butyl acrylate | propyl methacrylate |
| isobutyl acrylate | n-butyl methacrylate |
| hexyl acrylate | isobutyl methacrylate |
| octyl acrylate | hexyl methacrylate |
| n-decyl acrylate | octyl methacrylate |
| dodecyl acrylate | n-decyl methacrylate |
| hydroxyethyl methacrylate (HEMA) | dodecyl methacrylate |
| hydroxypropyl methacrylate | |
| hydroxybutyl methacrylate | |
| hydroxyisobutyl methacrylate | |
| hydroxyhexyl methacrylate | |
| hydroxyoctyl methacrylate | |
| hydroxy-n-decyl methacrylate | |
| hydroxydodecyl methacrylate. | |

It will obviously be understood that, insofar as said (meth)acrylic (co)polymer must be hydrophilic (in order to constitute said hydrogel), it is excluded that it be question of a methyl polymethacrylate (PMMA). When said methyl methacrylate (MMA) intervenes, it forcibly intervenes by way of comonomer.

The (meth)acrylic hydrophilic (co)polymer constituting the particles of the dispersed phase of the diphasic compositions of the invention, advantageously consists of cross-linked hydroxyethyl polymethacrylate (PHEMA) or, even more advantageously, of a cross-linked copolymer:

of hydroxyethyl methacrylate (HEMA) and
of ethyl methacrylate (EMA).

Said hydroxyethyl methacrylate (HEMA) gives the particles of the dispersed phase hydrophily and suppleness while said ethyl methacrylate (EMA) optimizes their mechanical properties. The quantity of intervention of said EMA must obviously remain within reasonable limits in order not to compromise the hydrophilic nature of the copolymer. It is specified here that said copolymer is advantageously obtained by copolymerization, for 100 parts by weight of monomers: HEMA+EMA, of 77.5 to 87.5 parts by weight (advantageously from 80 to 85 parts by weight) of HEMA and 12.5 to 22.5 parts by weight (advantageously from 15 to 20 parts by weight) of EMA. According to a particularly advantageous variant, it is obtained by copolymerization of 82.5 parts by weight of HEMA and 17.5 parts by weight of EMA.

In this way, the methacrylic copolymer which constitutes the particles of the dispersed phase of the diphasic compositions of the invention contain repeating units [HEMA] and repeating units [EMA] in a ratio R:R=[HEMA]/[HEMA], generally included between 3.0 and 6.1, advantageously included between 3.5 and 5 and, according to a preferred variant, being 4.1.

Said poly[HEMA/EMA] copolymer is, as specified hereinabove, cross-linked. Such a cross-linking is indispensable to ensure cohesion of the material and its stability. An (at least one) cross-linking agent—bifunctional—must therefore intervene, in an efficient quantity, during copolymerization of the HEMA and EMA monomers. This efficient quantity—generally, at maximum, some parts by weight: in principle included between 0.5 and 5 parts by weight, advantageously included between 0.5 and 2 parts by weight, for 100 parts by weight of HEMA+EMA monomers—must obviously remain reasonable. It is not a question of the intervening cross-linking agent constituting a comonomer and consequently modifying the properties, particularly the mechanical ones, of the poly(HEMA/EMA) copolymer.

In any case, the person skilled in the art is not unaware that the increase in the rate of intervening cross-linking agent reduces the water content of the hydrogels and increases their vitreous transition temperature.

It is indicated here that said cross-linking agent intervenes in the structure of the copolymer, generally in such a quantity that the ratio:

$$R' = \frac{\text{total number of reactive functions of said cross-linking agent present}}{\text{total number of reactive functions (methacrylates) of the reagents present (HEMA, EMA)}}$$

is included between $6.10^{-3}$ and $60.10^{-3}$. Said ratio R' is advantageously $10^{-2}$.

Concerning the reactive functions of said cross-linking agent, it is advantageously question of acrylate and/or methacrylate functions. The person skilled in the art knows numerous cross-linking agents performing such functions, and in particular:

butanediol dimethacrylate and diacrylate
hexanediol dimethacrylate and diacrylate
decanediol dimethacrylate and diacrylate
ethylene glycol dimethacrylate (EDMA)
tetraethylene glycol dimethacrylate.

Within the scope of the present invention, the intervention of the cross-linking agents listed hereinabove and more particularly that of EDMA, is recommended in non-limiting manner.

Thus, the poly(HEMA/EMA) copolymer constituting the particles of the dispersed phase of the diphasic compositions of the invention is cross-linked by cross-linking agents of this type (or of an equivalent type) of which trace is obviously found in its skeleton.

Said poly(HEMA/EMA) copolymer is prepared in manner known per se, by copolymerizing a mixture of HEMA and EMA monomers in the presence of efficient quantities of at least one polymerization initiator and at least one cross-linking agent.

It has been seen hereinabove that, concerning the cross-linking agent, an efficient quantity (generally from 0.5 to 5 parts by weight and advantageously from 0.5 to 2 parts by weight, for 100 parts by weight of monomers: HEMA+EMA), of a cross-linking agent such as EDMA, intervenes. Said EDMA may intervene in particular at the rate of 0.8 part by weight. Other cross-linking agents as indicated hereinabove, may intervene in place of said EDMA.

By way of initiator of the radical HEMA-EMA copolymerization, the following may in particular be used:

- a mixture of sodium phosphite and sodium phosphate (or any other oxidoreduction couple);
- an azo compound such as azobisisobutyronitrile (AIBN) or (2,2'-azobis (2,4-dimethyl valeronitrile)(AIVN), in particular marketed by WAKO under reference V65, of which the developed formulae are reproduced hereinbelow:

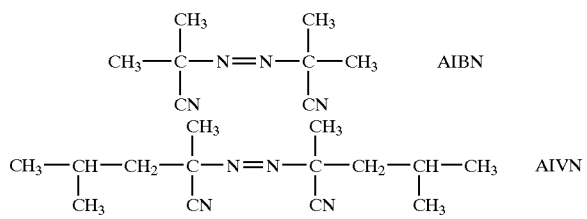

This latter compound is particularly preferred in view of its low toxicity, as well as that of its products of degradation. (However, it will be generally noted that said polymerization initiator intervenes in a very small quantity and is generally eliminated at the end of the method for preparing the hydrogel);

- a peroxide such as benzoyl peroxide.

The person skilled in the art knows how to master the quantity of intervention of said radical polymerization initiator (generally less than 1 part by weight for 100 parts by weight of monomers: HEMA+EMA) and, in general. the kinetics of polymerization of the reactional mixture. In particular, he knows that, as oxygen neutralizes the action of said polymerization initiator, it is highly preferable to eliminate it from the reactional mixture before the rise in temperature. A bubbling-through of inert gas of said reactional mixture is highly recommended. Concerning the heating programme, its optimalization is within the scope of the person skilled in the art.

Said cross-linked poly(HEMA+EMA) copolymer is therefore largely recommended by way of material constituting the particles of the dispersed phase of the diphasic compositions of the invention.

The precisions given hereinabove with reference to the preparation of said copolymer, particularly those relative to the nature of the cross-linking agent(s) and polymerization initiator(s) likely to intervene, are obviously applicable to the context of the (co)polymerization and cross-linking of monomers of other natures for the preparation of other polymers or copolymers suitable for constituting the particles of the dispersed phase.

Within the diphasic compositions of the invention. the particles of the dispersed phase generally intervene at a rate of 10 to 30% by mass, advantageously at a rate of 15 to 25% by mass. Generally, one has:

$$10\% \leq \frac{\text{mass of the dispersed phase}}{\text{mass of the dispersed phase} + \text{mass of the continuous phase}} \leq 30\%.$$

The continuous phase is considered hydrated, while the dispersed phase may be considered dry or at equilibrium. Advantageously, in this type of ratio, the dry mass of the dispersed phase, i.e. the dry mass of the particles, is considered.

It is specified here that a single type of particles generally intervenes within the dispersed phase. However, it is in no way excluded from the scope of the invention to employ particles of different shape and/or nature . . . , conjointly.

Concerning the preparation of the diphasic compositions of the invention, the person skilled in the art has already understood that it does not raise particular difficulties. Said preparation, which constitutes the second object of the present invention, comprises:

- the preparation of the continuous phase (advantageously that of a hydrogel of cross-linked hyaluronic acid);
- the preparation of the dispersed phase (particles of at least one hydrogel of a (co)polymer obtained by polymerizing and cross-linking acrylic acid and/or methacrylic acid and/or at least one derivative of said acids);
- the incorporation and the mixture in said continuous phase of said dispersed phase.

The preparation of the continuous phase and in particular that of a hydrogel of cross-linked hyaluronic acid, advantageously at the rate of cross-linking and at the concentration of acid specified hereinabove, does not raise any particular difficulty.

Similarly, the particles of the dispersed phase may be obtained by any method known per se. Particles with symmetry of revolution, with smooth surface, and in particular microspheres, may be obtained by emulsification.

It has been seen that it was recommended to prepare fragments with rough surface; said fragments being advantageously obtained by mechanically crushing an appropriate mass of hydrogel.

Within the framework of the method of the invention, it is advantageously recommended to prepare the particles of the dispersed phase, to dry them and to add them, dried, to the continuous phase.

The prepared diphasic composition is advantageously sterilized for storage. It is recommended to pack it, before sterilization and storage. It is advantageously packed in syringes. It is in that case ready for use.

In accordance with its final object, the invention therefore relates to a filling material, useful in reparative surgery and in plastic surgery, based on the diphasic compositions such as described hereinabove.

Said material is particularly high-performance, in particular in terms of stability and non-traumatizing nature, due to the nature and consistency of its continuous phase (advantageously cross-linked HA) and dispersed phase (hydrogel).

The use of such a filling material is recommended for filling in particular wrinkles of the face such as the glabellar wrinkle, the peri-buccal wrinkles, the naso-genial furrows, for attenuating crowsfeet . . .

The invention is illustrated by the following example.

A diphasic composition of the invention was prepared from fibers of sodium hyaluronate (NaHa) for the continuous phase and from fragments of a poly[HEMA/EMA] hydrogel for the dispersed phase.

a) Preparation of the Continuous Phase

Said continuous phase is prepared with fibers of sodium hyaluronate (of molecular mass: $M_w \approx 2.9 \ 10^6$ Da), of bacterial origin. An 11.5% by mass solution of said fibers in 0.25 M sodium hydroxide is firstly prepared.

To said homogenized solution. 60 μl of 1,4-butanediol diglycidyl ether (BDDE) are added. The mixture obtained, homogenized, is placed in a water bath at 50° C. for 2 hours.

The resultant gel is then neutralized by the addition of 1M hydrochloric acid, then diluted by phosphate buffer at pH 7.2 until a concentration of NaHa of 20 mg/g is obtained.

This gel is then purified by dialysis in a phosphate buffer bath in order to eliminate from its structure both the cross-linking agent (BDDE) and the polymer which have not reacted.

Within such a gel, the ratio: total number of reactive functions of said cross-linking agent/total number of disaccharide repeating units of the molecules of the polymer present, is 0.27.

b) Preparation of the Dispersed Phase

Discs or sticks of an acrylic hydrogel were prepared in a first step, as follows:

82.5 g of hydroxyethyl methacrylate (HEMA), 17.5 g of ethyl methacrylate (EMA), 1 g of 4-methacryloxy-2-hydroxybenzophenone (MOBP), 0.8 g of ethylene glycol dimethacrylate (EDMA) and 0.2 g of benzoyl peroxide, were poured in a beaker.

The reactional mixture was homogenized then argon was bubbled through for 2 mins. The solution thus deoxygenated was then distributed in moulds; said moulds were then placed:

48 hours in a water bath at 40° C.;
48 hours in a water bath at 60°:
then 48 hours in an oven at 100° C.

The material obtained, after cooling, was demoulded.

The demoulded discs or sticks were then mechanically crushed. The powder thus obtained was successively sieved over sieves of mesh 100, 40 and 25 μm. Only the fragments recovered on the 25 μm sieve were kept. They were then purified in an ebullient alcohol/water bath, left to decant in order to eliminate the small fragments possibly remaining on the 25 μm sieve, and finally rinsed in two successive baths of deionized water. After drying, under flux (class 100), of the fragments thus obtained, they were again sieved over 25 μm, before being used for the final product.

c) Preparation of the Diphasic Composition 11 g of dry fragments, as obtained in point b), are added to the cross-linked gel of NaHa, as obtained in point a). The whole is mixed in order to obtain a homogeneous dispersion. The mass ratio m=mass of the fragments/(mass of the fragments+gel mass), is 0.2.

Samples of said diphasic composition obtained were in particular subjected to tests of extrudability, with a view to characterizing the force necessary for its injection. Said tests were carried out with the aid of a VERSATEST (MECMESIN) traction apparatus.

For a speed of compression of 12.5 mm/min., the characteristic force of the injection through:

a needle of 30 G ½ is 25 to 30 N,
a needle of 27 G ½ is 12 to 15 N.

d) Packing of the Diphasic Composition

The dispersion or suspension obtained is placed in syringes which are sterilized in an autoclave. Said dispersion is injectable, in particular through needles of 25 G to 30 G ½.

What is claimed is:

1. A biocompatible diphasic composition comprising a dispersed phase and a continuous phase, said dispersed phase residing in suspension in said continuous phase, wherein said dispersed phase consists of particles of at least one hydrogel of a polymer/copolymer obtained by polymerizing and cross-linking acrylic acid, methacrylic acid and/or at least one derivative of said acids; and wherein said continuous phase is an aqueous solution or hydrogel of at least one polymer selected from proteins, polysaccharides and their derivatives, which has been cross-linked.

2. The composition according to claim 1, wherein said continuous phase is a hydrogel of a cross-linked polysaccharide selected from hyaluronic acid, its salts and mixtures of its salts.

3. The composition according to claim 1, wherein said continuous phase is a hydrogel of cross-linked polysaccharide which is sodium hyaluronate.

4. The composition according to claim 2, wherein the hydrogel constituting said continuous phase is obtained from said polysaccharide whose molecular mass is greater than or equal to 1 million Daltons, which was cross-linked, via its hydroxy functions, by means of a cross-linking agent, at a cross-linking rate defined by the ratio: total number of reactive functions of said cross-linking agent/total number of disaccharide repeating units of the molecules of said polysaccharide, wherein said ratio is between 0.25 and 0.50.

5. The composition according to claim 4, wherein said polysaccharide has molecular mass ranging between 2 and 4 million Daltons.

6. The composition according to claim 2, wherein the hydrogel constituting said continuous phase contains said cross-linked polymer at a concentration ranging between 10 and 25 mg/g.

7. The composition according to claim 2, wherein the hydrogel constituting said continuous phase contains said cross-linked polymer at a concentration ranging between 15 and 25 mg/g.

8. The composition according to claim 2, wherein said polymer of said hydrogel is produced by bacteria.

9. The composition according to claim 1, wherein said particles of said dispersed phase have a largest dimension ranging between 10 and 120 μm.

10. The composition according to claim 1, wherein said particles of said dispersed phase have a largest dimension ranging between 20 and 80 μm.

11. The composition according to claim 1, wherein said particles of said dispersed phase are fragments having a rough surface obtained by crushing a mass of hydrogel.

12. The composition according to claim 1, wherein said particles of said dispersed phase have a water content, at equilibrium, ranging between 10 and 40% by weight.

13. The composition according to claim 1, wherein said particles of said dispersed phase have a water content, at equilibrium, of about 25% by weight.

14. The composition according to claim 1, wherein said dispersed phase consists of hydrogel particles of a cross-linked copolymer of hydroxyethyl methacrylate (HEMA) and of ethyl methacrylate (EMA).

15. The composition according to claim 14, wherein said cross-linked copolymer contains the repeating HEMA and EMA units in a ratio $$R = \frac{HEMA}{EMA};$$

said ratio R being included between 3.0 and 6.1.

16. The composition according to claim 15, wherein said ratio R is included between 3.5 and 5.

17. The composition according to claim 15, wherein said ratio is 4.1.

18. The composition according to claim 14, wherein said cross-linked copolymer is obtained by reaction, for 100 parts by weight of monomers: HEMA+EMA, of:

77.5 to 87.5 parts by weight of HEMA, and 12.5 to 22.5 parts by weight of EMA;

in the presence of an efficient quantity of at least one cross-linking agent.

19. The composition according to claim 14, wherein said cross-linked copolymer is obtained by reaction, for 100 parts by weight of monomers: HEMA+EMA, of:

80 to 85 parts by weight of HEMA, and 15 to 20 parts by weight of EMA;

in the presence of an efficient quantity of at least one cross-linking agent.

20. The composition according to claim 1, wherein it contains from 10 to 30% by mass of said particles in suspension in said continuous phase.

21. The composition according to claim 1, wherein it contains from 15 to 25% by mass of said particles in suspension in said continuous phase.

22. A method for preparing a composition according to claim 1, comprising:

a. cross-linking an aqueous solution of at least one polymer selected from proteins, polysaccharides and their derivatives to obtain the continuous phase;

b. obtaining particles of at least one hydrogel resulting from the polymerization and cross-linking of acrylic acid, methacrylic acid and/or one derivative of said acids;

c. optionally drying the said particles; and d. incorporating and mixing the said particles in said continuous phase.

23. The method according to claim 22, wherein the said particles are obtained by mechanically crushing a mass of the hydrogel.

24. A method of reparative surgery or plastic surgery, comprising using the biocompatible diphasic composition according to claim 1 as a filling material.

* * * * *